(12) United States Patent
McDougall et al.

(10) Patent No.: US 9,035,097 B2
(45) Date of Patent: May 19, 2015

(54) AMINOETHYLATION PROCESS HAVING IMPROVED YIELD OF ARYLOXYALKYLENE AMINE COMPOUNDS AND REDUCED UREA BY-PRODUCTS

(75) Inventors: Patrick J. McDougall, Farifax, CA (US); James Saenz, Napa, CA (US); David Lao, San Ramon, CA (US)

(73) Assignee: Chevron Oronite Company LLC, San Ramon, CA (US)

( * ) Notice: Subject to any disclaimer, the term of this patent is extended or adjusted under 35 U.S.C. 154(b) by 190 days.

(21) Appl. No.: 13/612,595

(22) Filed: Sep. 12, 2012

(65) Prior Publication Data
US 2014/0073814 A1    Mar. 13, 2014

(51) Int. Cl.
C07C 215/00 (2006.01)
C07C 209/78 (2006.01)
C07C 213/08 (2006.01)

(52) U.S. Cl.
CPC ............. *C07C 209/78* (2013.01); *C07C 213/08* (2013.01)

(58) Field of Classification Search
None
See application file for complete search history.

(56) References Cited

U.S. PATENT DOCUMENTS

| 2,517,750 | A | 8/1950 | Wilson |
| 6,384,280 | B1 | 5/2002 | Cherpeck |
| 6,486,352 | B1 | 11/2002 | Gray |
| 6,649,800 | B1 | 11/2003 | Gray |

OTHER PUBLICATIONS

PCT/US13/49863, International Search Report, Mail date Dec. 3, 2013, 3 pages.

*Primary Examiner* — Clinton Brooks
(74) *Attorney, Agent, or Firm* — Joseph P. Foley

(57) ABSTRACT

Disclosed is a process for preparing an aryloxyalkylene amine compound via an aminoethylation reaction comprising: a) reacting an aromatic hydroxyl compound in the presence of a basic catalyst with a 2-oxazolidinone compound of the formula II to form an intermediate reaction product;

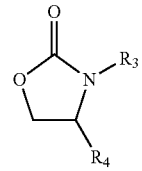

Formula II wherein $R_3$ is selected from the group consisting of hydrogen or lower alkyl having 1 to 6 carbon atoms, $R_4$ is selected from the group consisting of hydrogen, straight or branched chain alkyl having from one to six carbon atoms, phenyl, alkaryl, or arylalkyl; and b) reacting the intermediate product of step a) with a polyalkylene polyamine.

14 Claims, No Drawings

AMINOETHYLATION PROCESS HAVING IMPROVED YIELD OF ARYLOXYALKYLENE AMINE COMPOUNDS AND REDUCED UREA BY-PRODUCTS

FIELD OF INVENTION

This invention is directed to an improved aminoethylation reaction process for producing aryloxyalkylene amine compounds in higher yield by facilitating the in-situ reaction of ureaH by-products with a polyalkylene polyamine.

BACKGROUND

Aryloxyethylene amine compounds are known as useful intermediates and find application in pharmaceuticals and pesticides, among other uses. For example, U.S. Pat. No. 2,133,779 discloses such compounds are useful as antioxidants in vulcanized rubber compounds. U.S. Pat. Nos. 4,792,570; 4,536,503; and 4,792,551 disclose that certain biphenyloxyaminoalkanes, naphthoxyalkylamines, and 9-anthryloxyaminoalkanes have anti-inflammatory and analgesic activity; typically these compounds are prepared through an aryloxyalkylhalide intermediate. U.S. Pat. No. 7,081,465 discloses certain naphthyloxyaminoalkyane compounds for use as antihyperglycemic agents prepared by reacting naphthol with a dihaloalkane in the presence of a base to form a naphthoxyalkylene halide intermediate which is further reacted with an amine in the presence of an acid binding agent.

U.S. Pat. No. 5,030,755 discloses a method of preparing a phenoxyethylamine by reducing a substituted phenoxyacetaldehyde oxime with hydrogen in the presence of a Raney-nickel catalyst.

German Patent Publication DE 19711004 A1 discloses the use of 2-oxazolidinone to prepare phenoxyaminoalkanes from low molecular weight phenols; namely, 2-4-(Phenoxyphenoxy) ethylamine and ethyl 2-(phenoxyphenoxy)ethyl-carbamate are sequentially prepared in high yield and selectivity by the aminoethylation of 4-phenoxyphenol with 2-oxazolidinone under inert atmosphere, followed by amidation of 2-4(phenoxyphenoxy)ethylamine with carbonate derivatives.

Japanese Patent Publication No. JP 2592732 B2 discloses a method of producing phenoxyethylamines by reacting, under base conditions, low molecular weight phenols and 2-oxazolidinone. It states that phenoxyethylamines are important raw materials for pharmaceuticals and pesticides.

U.S. Pat. Nos. 6,384,280 and 6,649,800 teach the use of 2-oxazolidinone or a derivative thereof in aminoethylation transformations involving high molecular weight polyalkylphenols to provide polyalkylphenoxyaminoalkanes of the type disclosed in U.S. Pat. Nos. 5,669,939 and 5,851,242. A process for preparing the 2-oxazolidinone in-situ for aminoethylation of polyalkylphenols to polyalkyphenoxyaminoalkanes is disclosed in U.S. Pat. No. 6,486,352. Their use as an intermediate in the preparation of fuel additives has been described in U.S. Pat. No. 6,114,542 in the preparation of polyalkyl or polyalkenyl N-hydroxyalkyl succinimides from various aryloxyalkene amines and polylakyl or polyalkenyl succinic anhydrides was disclosed, along with their use in fuel compositions.

The processes above typically have poor yields and/or employ undesirable reactants or by-products in the reaction mixture which require further separation. The modified process of the present invention enables one to achieve exceptionally high conversion of an aromatic hydroxyl compound—starting material, into the desired aryloxyalkylene amine products. This process also eliminates the need to dispose of large quantities of unwanted by-products. The process is readily amenable to manufacturing and incurs a minimal cost increase over the previously reported methods.

SUMMARY

Accordingly, an aspect of the present invention is directed to a process for preparing an aryloxyalkylene amine compound via an aminoethylation reaction comprising: a) reacting an aromatic hydroxyl compound in the presence of a basic catalyst with a 2-oxazolidinone compound of the formula II to form an intermediate reaction product;

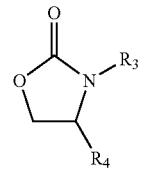

Formula II wherein $R_3$ is selected from the group consisting of hydrogen or lower alkyl having 1 to 6 carbon atoms, $R_4$ is selected from the group consisting of hydrogen, straight or branched chain alkyl having from one to six carbon atoms, phenyl, alkaryl, or arylalkyl; and b) reacting the intermediate product mixture of step a) with a polyalkylene polyamine. In this regard the intermediate product mixture contains at least one dialkylene urea compound which may react with the polyalkylene polyamine. Thus, in a preferred aspect, at least one dialkylene urea comprises an N,N'-bis(aryloxyalkylene)urea. In this regard, the N,N'-bis(aryloxyalkylene)urea is derived from the aromatic hydroxyl compound. In one aspect, the intermediate product of step a) contains a dialkylene urea moiety in an amount from 10 to 50 mole %, more particularly the intermediate product of step a) contains an N,N'-bis(aryloxyalkylene)urea moiety in an amount from 10 to 50 mole %.

One aspect of the invention is directed to improved conversion of the aromatic hydroxyl compound reactant, thus this aspect employs the 2-oxazolidinone compound reactant in molar excess to the aromatic hydroxyl compound. In this regard, the molar ratio of aromatic hydroxyl compound to 2-oxazolidinone compound of formula II in step a) is from 1:2 to 1:1.2 The 2-oxazolidinone compound of formula II may be formed in-situ by reacting a β-amino alcohol of the formula $NH_2$—$CHR_{10}CH_2$—OH wherein $R_{10}$ is a lower alkyl having 1 to 6 carbon atoms, phenyl, alkaryl, or arylalkyl; with a dialkyl carbonate of the formula $(R_{11}O)_2CO$ where $R_{11}$ is lower alkyl having 1 to about 6 carbon atoms. Suitable polyalkylene polyamine are of the formula $H_2N$-A-$(N[R_5]$-A$)_x$-$NR_6R_7$, wherein x is an integer of from about 0 to 10, A is an alkylene radical from 2 to 10, $R_5$, $R_6$ and $R_7$ are independently selected from hydrogen, an alkyl from 1 to 6 carbon atoms group, more particularly A may be selected from ethylene, 1,2-propylene and 2-2-dimethylpropylene.

Another aspect is directed to a method for improving the yield of an aryloxyalkylene amine compound prepared via an aminoethylation reaction comprising: a) reacting an aromatic hydroxyl compound in the presence of a basic catalyst with a 2-oxazolidinone compound of the formula II to form an intermediate reaction product;

Formula II

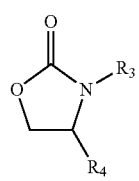

wherein $R_3$ is selected from the group consisting of hydrogen or lower alkyl having 1 to 6 carbon atoms, $R_4$ is selected from the group consisting of hydrogen, straight or branched chain alkyl having from one to six carbon atoms, phenyl, alkaryl, or arylalkyl; and thereafter b) reacting the intermediate product of step a) with a polyalkylene polyamine. In this regard the intermediate product contains at least one N,N'-bis(aryloxyalkylene) urea compound. This may be further optimized, wherein during the reaction in step a) the concentration of aromatic hydroxyl compound or the concentration of at least one N,N'-bis(aryloxyalkylene)urea compound is monitored. Thus for example the concentration of at least one N,N'-bis(aryloxyalkylene)urea compound is monitored wherein the amount of polyalkylene amine is adjusted to convert the compound monitored into the aryloxyalkylene amine, thereby leading to improved product yields.

DETAILED DESCRIPTION

Disclosed is a process for preparing an aryloxyalkylene amine compound comprising reacting an aromatic hydroxyl compound in the presence of a basic catalyst with a 2-oxazolidinone compound to form an intermediate reaction product mixture containing at least a portion of a dialkylene urea compound; and thereafter reacting the intermediate reaction product with a polyalkylene polyamine; whereby at least a portion of the dialkylene urea compound is converted to the desired aryloxyalkylene amine compound. Commonly the dialkylene urea compound is an N,N'-bis(aryloxyalkylene) urea derived from the aromatic hydroxyl compound. The process is particularly suited in instances where high purity aryloxyalkylene amine compounds are desired and results in high conversion of the reactant aromatic hydroxyl compound to the aryloxyalkylene amine. In this regard, the process for preparing an aryloxyalkylene amine compound via aminoethylation reaction comprising reacting an aromatic hydroxyl compound in the presence of a basic catalyst with a 2-oxazolidinone compound of the formula II to form an intermediate reaction product mixture; and thereafter reacting the intermediate reaction product with a polyalkylene polyamine can performed in a single reactor. Such "one pot" or single reactor reaction can advantageously be employed to convert at least a portion of the N,N'-bis(aryloxyalkylene)urea by-product to the desired aryloxyalkylene amine by reaction with a polyalkylene polyamine and resulting urea exchange reaction.

To exemplify, the conversion of 2-naphthol to the 2-aminoethoxynaphthalene ("2-AEN") with 2-oxazolidinone under base catalyzed conditions was studied utilizing known methods. All major and minor by-products were separated and analyzed using techniques known to those skilled in the art. In addition to forming the aryloxyalkylene amine product (I), N,N'-bis(2-(2-naphthoxy)ethyl)urea (II), and a related imidazolidinone (III) were formed as major by-products (See Products Scheme A). Typical product fractions were 65-70 mol % I, 20-30 mol % II, and 5-10 mol % imidazolidinone III. We also noted significant amounts of ethanolamine formed during the reaction (collected in Dean-Stark trap).

Products Scheme A. Major products of the 2-oxazolidinone process

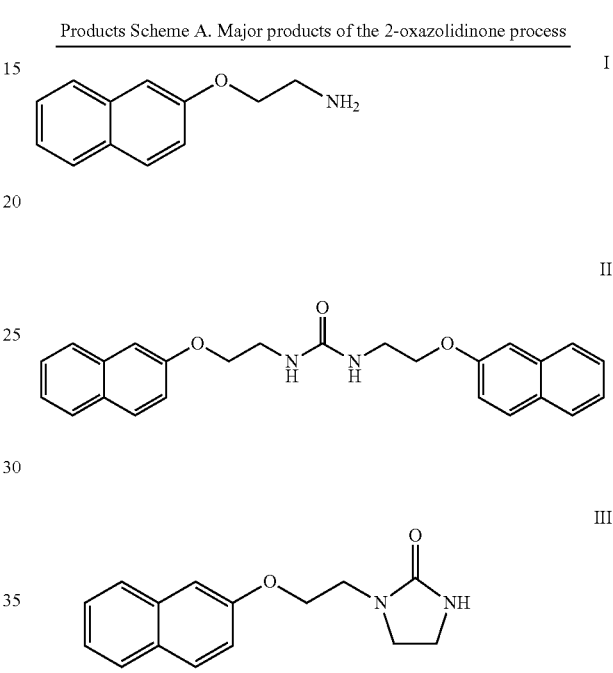

Although not bound by any applicable theory, below is outlined a possible mechanistic pathway for the aminoethylation reaction of a base catalyzed reaction of an aromatic hydroxyl compound with 2-oxazolidinone. The reaction is outlined using 2-naphthol and unsubstituted 2-oxazolidinone merely for simplicity of illustration; however other substituent groups as defined herein on the aromatic hydroxyl compound and/or 2-oxazolidinone reactants are expected to be equivalent in the reaction mechanism. Thus, the methodology summarized herein below is expected to applicable for the aminoethylation reaction of a base catalyzed reaction of an aromatic hydroxyl compound with 2-oxazolidinone disclosed.

As outlined below in Part A of Scheme 1, the formation of aminoethoxy aromatics such as 2-aminoethoxy naphthalene ("2-AEN") (I) begins with the nucleophilic attack of potassium naphthoxide to the ethylene carbon of 2-oxazolidinone (reaction pathway A) to form the short-lived carbamate intermediate. This intermediate (not observed) quickly decarboxylates to evolve carbon dioxide gas and the desired product, 2-AEN (I). This step is essentially irreversible due to the escape of carbon dioxide through the nitrogen outlet line. Although plausible, the alternate carbamate shown via reaction pathway B was not observed in detectable quantities.

Scheme 1. Proposed mechanism of the synthesis of 2-AEN and by-products

Part A.

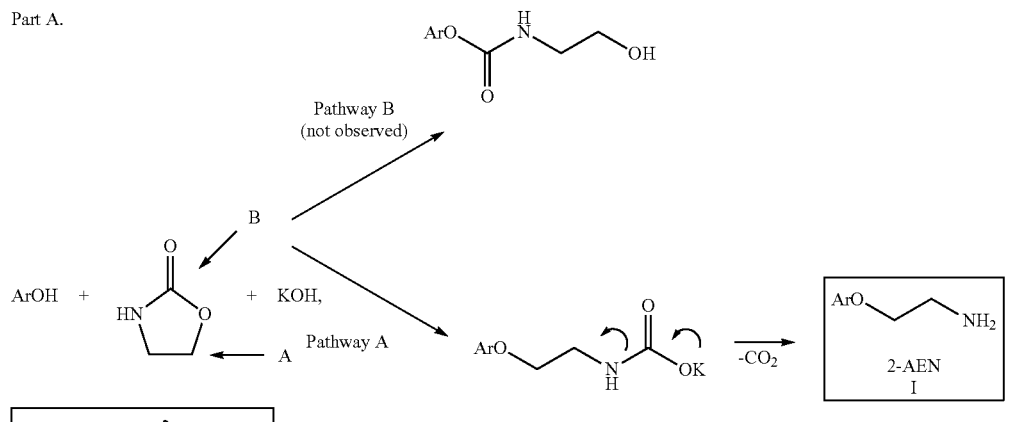

Part B.

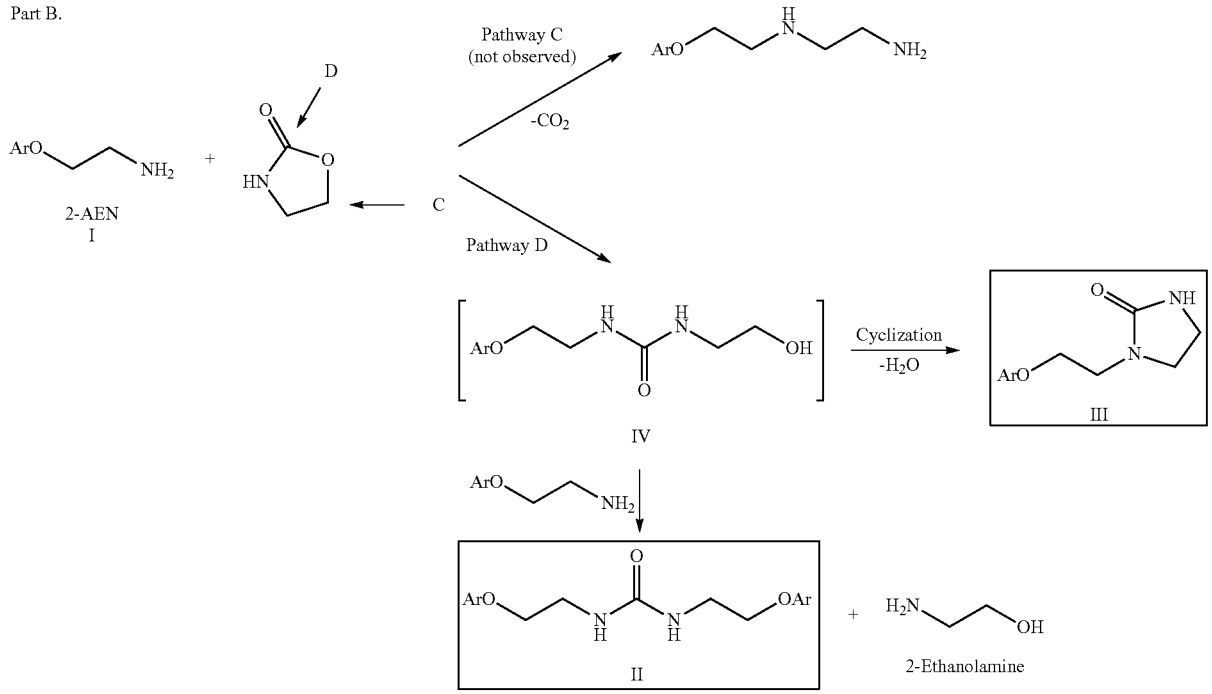

As can be seen in Part B of Scheme 1, 2-AEN will compete with 2-naphthol by reacting with 2-oxazolidinone to form the two major by-products N,N'-bis(2(2-naphthoxy)ethyl)urea II (also referred to herein as a dialkylene urea since the urea moiety is bonded to substituted alkyl groups, more typically one or aryloxy groups which may be the same "bis" or different) and a related imidazolidinone (also referred to herein as a cyclic urea) III. It is postulated that these products are both derived from the unstable asymmetrical urea IV arising from attack of the amine of 2-AEN to the carbonyl carbon of 2-oxazolidinone (pathway D). Although asymmetrical urea IV was not observed as a product of the reaction, it was proposed that this intermediate readily reacts to form the two different thermally stable by-products under the reaction conditions. First, asymmetrical urea IV can react in an intramolecular fashion to form the imidazolidinone III through the loss of water. Reports of this type of intramolecular reaction occurring have been published (See J. Org. Chem. 1992, 57, 6257). Alternatively, the asymmetrical urea IV can react with another equivalent of 2-AEN to form symmetric urea II and 2-ethanolamine. Based on the isolated product ratios, the formation of II is the favored fate of the asymmetrical urea IV. The aminoethylation of amine I through reaction Pathway C was not observed.

The formation of the N,N'-bis(aryloxyalkylene)urea by-product (such as II) can significantly lower the yield of desired aryloxy ethyleneamine product since the desired product is consumed in the process. In addition, the presence of this by-product adds to the purification steps needed, contributes to waste generation and disposal, and may have solubility concerns depending upon the application. Although this N,N'-bis(aryloxyalkylene)urea by-product could ultimately be removed from the reaction product mixture for example by an additional filtering step, an improved method was sought to recover the desired product directly from this by-product.

Literature suggests that various methods exist for the liberation of the free amine from ureas, including acid hydrolysis (see for example, J. Org. Chem. 1990, 55, 5017) base hydrolysis (see for example, J. Chem. Soc. Perkin Trans. 11990, 2, 375) and hydrogenation (see for example Angew. Chem. Int. Ed. 2011, 50, 11702). These methods however, were not amenable to a one-pot procedure nor particularly attractive for large scale manufacturing. Thus, the alkylene polyamine post treatment of the aminoethylation intermediate reaction product mixture was developed whereby the alkylene polyamine could react at least a portion of dialkylene urea reaction by-product to the desired aryloxy-alkylene amine product.

The conversion of the dialkylene urea II to 2-AEN (I) was demonstrated by treatment with 1,2-diamine compounds, such as ethylenediamine (EDA), which was shown to exchange for the 2-AEN and form the more thermodynamically stable 2-imidazolidinone. In a model experiment, treatment of symmetric urea II with equimolar amounts of ethylenediamine (EDA) in a suitable solvent such as C9 solvent at reflux temperature resulted in the conversion to 2-imidazolidinone (V) and the desired product 2-AEN (I) in 76% yield (Scheme 2).

Scheme 2. Conversion of N,N'-bis(2-(2-napthoxy)ethyl) Urea to 2-AEN

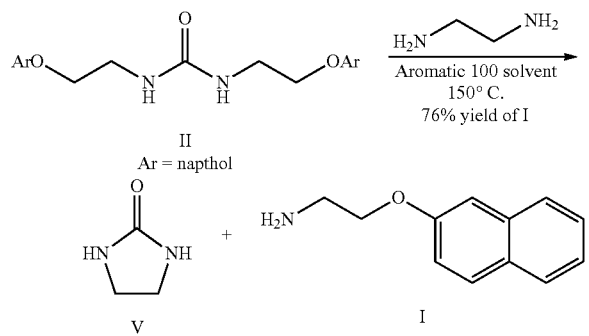

In practice, once the aromatic hydroxy compound has been suitably converted to products one can simply add the diamine to the reaction mixture to essentially convert all of the dialkylene urea into the desired product. Using this procedure, yields have shown to dramatically improve, for example, from 65% to >95%. In this regard, suitable conversion of the aryl hydroxyl compound to the desired aryloxy alkyleneamine product is greater than 50%, preferably greater than 75%, more preferably greater than 85% and up to 95%.

Other diamines are also useful in this process such as other 1,2-diamines and/or 1,3-diamines which are readily available, such as diethylenetriamine (DETA), triethylenetriamine (TETA) and heavy polyamine (HPA). These amines also required less reaction time due to the higher temperatures that could be achieved.

Aryloxyalkylene Amine

The aryloxy-alkylene amine product is suitably an alkylene mono primary amine. The alkylene group comprises straight and branched chain alkylene groups having 2 to 18 carbon atoms having an ethylene linkage or a beta substituted ethylene linker, wherein the substituent groups are lower alkyl selected from 1 to 6 carbon atoms, aryl, alkaryl and arylalkyl more preferably selected from phenyl and benzyl. The aromatic core moiety is meant to include both mononuclear and polynuclear groups wherein the mononuclear and polynuclear groups may optionally be substituted with one to three substituents. The polynuclear groups can be of the fused type wherein the aromatic nuclear is fused at two points to another nucleus such as found in naphthyl or anthranyl groups. The aromatic may also be the linked type wherein at least two nuclei (either mononuclear or polynuclear) are linked through bridging linkages to each other. These bridging linkages can be chosen from, among others known to those skilled in the art, direct carbon to carbon bonds between the groups without any intervening atoms, alkylene linkages, ether linkages, ester linkages, keto linkages, sulfur linkages and the like. In a preferred aspect, the aromatic group contains at least two aromatic groups either fused or linked. Examples of particularly suited aromatic core groups are derived from benzene, naphthylene and anthracene containing carboxylic groups wherein the aromatic core group is differentiated from an optional substituent. Each of these various aromatic groups may also be substituted by various substituents, including hydrocarbyl substituents.

In a general aspect, the aryloxy-alkylene amine is of the formula Ar—O-Alk-NH$_2$ wherein Ar is an aromatic moiety selected from benzene, naphthylene or anthracene or optionally substituted benzene, optionally substituted naphthylene or optionally substituted anthracene, with the optionally substituted groups selected from 1 to 3 substituent groups selected from alkyl, alkoxy, aryl, alkaryl, arylalkyl, aryloxy, wherein preferably alkyl is straight or branched chain carbon having less than 8 carbon atoms and more preferably alkyl is from $C_1$ to $C_6$. When the substituent group is aryl, alkaryl, arylalkyl, aryloxy the aromatic groups may be referred to as linked. Particularly preferred aryl groups are phenyl or naphthyl. Preferred arylalkyl groups include the groups in which one hydrogen of the alkyl group is substituted with an aryl group and include, for example benzyl, phenethyl, phenpropyl, napthylmethyl, naphthylethyl, naphthylpropyl. Preferred aryloxy groups include phenoxy and naphthyloxy particularly 1-naphthyloxy and 2-naphthyloxy. The -Alk- group comprises straight and branched chain alkylene groups having 2 to 10 carbon atoms, with ethylene, beta substituted ethylene, wherein the substituent groups are lower alkyl selected from 1 to 6 carbon atoms, phenyl and benzyl.

The preferred alkylene group comprises ethylene and beta substituted ethylene (in this regard, beta is in reference to the oxygen of Ar—O— group. In one aspect, Alk is —CH$_2$CH(R$_o$)— wherein R$_o$ is selected from the group consisting of hydrogen, a straight or branched chain alkyl from $C_1$ to $C_6$, phenyl or a benzyl group e.g. a phenylmethylene group.

A preferred Ar—O— group is derived from an aromatic hydroxyl compound of the formula:

Formula I

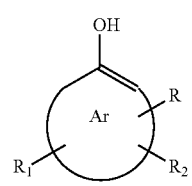

Wherein Ar is an aromatic ring (arene), an optionally substituted aromatic hydrocarbon and may be monocyclic or polycyclic; $R_1$, $R_2$ and R are each independently represent a hydrogen atom or organic group, wherein the number of carbon atoms that compose the aromatic hydroxyl compound is an integer of from 6 to 50, and wherein $R_1$ and $R_2$ may bond with Ar to form a multi-ring structure. Examples of substituent's that substitute the aromatic moiety of an aromatic hydroxyl compound may include the groups comprising hydrogen, an alkyl group, a cycloalkyl group, an aryl group, an arylalkyl group, an ether group (substituted and/or unsubstituted alkyl ether group and/or aryl ether and/or arylalky ether), and a keto or thio group. Examples of suitable aromatic rings Ar may include a benzene ring, a naphthalene ring, an anthracene ring, a phenanthrene ring, a naphthacene ring, a chrysene ring, a pyrene ring, a triphenylene ring, a pentalene ring, an azulene ring, a heptalene ring, an indacene ring, a biphenylene ring, an acenaphthylene ring, an aceanthrylene ring and an acephenanthrylene ring. More preferably, the aromatic ring Ar has a structure that contains at least one structure selected from a benzene ring and/or a naphthalene ring.

Suitable $R_1$, $R_2$, and R groups may independently include: hydrogen, alkyl groups and/or cycloalkyl groups and/or cycloalkyl groups substituted with an alkyl group and/or alkyl groups substituted with a cycloalkyl group such as a methyl group, an ethyl group, a propyl group (including isomers), a butyl group (including isomers), a pentyl group (including isomers), a hexyl group (including isomers), a heptyl group (including isomers), an octyl group (including isomers), a nonyl group (including isomers), a decyl group (including isomers), a dodecyl group (including isomers), an octadecyl group (including isomers), cyclopentyl group, cyclohexyl group, cycloheptyl group, cyclooctyl group, methylcyclopentyl group (including isomers), ethylcyclopentyl group (including isomers), methylcyclohexyl group (including isomers), ethylcyclohexyl group (including isomers), propylcyclohexyl group (including isomers), butylcyclohexyl group (including isomers), pentylcyclohexyl group (including isomers), hexylcyclohexyl group (including isomers), dimethylcyclohexyl group (including isomers), diethylcyclohexyl group (including isomers) or dibutylcyclohexyl group (including isomers); alkoxy groups and/or cycloalkoxy groups and/or cycloalkoxy groups substituted with an alkoxy group and/or alkoxy groups substituted with a cycloalkoxy group such as a methoxy group, an ethoxy group, a propoxy group (including isomers), a butyloxy group (including isomers), a pentyloxy group (including isomers), a hexyloxy group (including isomers), a heptyloxy group (including isomers), an octyloxy group (including isomers), a nonyloxy group (including isomers), a decyloxy group (including isomers), a dodecyloxy group (including isomers), an octadecyloxy group (including isomers), a cyclopentyloxy group (including isomers), a cyclohexyloxy group (including isomers), a cycloheptyloxy group (including isomers), a cyclooctyloxy group (including isomers), a methylcyclopentyloxy group (including isomers), an ethylcyclopentyloxy group (including isomers), a methylcyclohexyloxy group (including isomers), an ethylcyclohexyloxy group (including isomers), a propylcyclohexyloxy group (including isomers), a butylcyclohexyloxy group (including isomers), a pentylcyclohexyloxy group (including isomers), a hexylcyclohexyloxy group (including isomers), a dimethylcyclohexyloxy group (including isomers), a diethylcyclohexyloxy group (including isomers), or a dibutylcyclohexyloxy group (including isomers); substituted or unsubstituted aryl groups such as a phenyl group, a methylphenyl group (including isomers), an ethylphenyl group (including isomers), a methylphenyl group (including isomers), an ethylphenyl group (including isomers), a propylphenyl group (including isomers), a butylphenyl group (including isomers), a pentylphenyl group (including isomers), a hexylphenyl group (including isomers), a heptylphenyl group (including isomers), an octylphenyl group (including isomers), a nonylphenyl group (including isomers), a decylphenyl group (including isomers), a biphenyl group (including isomers), a dimethylphenyl group (including isomers), a diethylphenyl group (including isomers), a dipropylphenyl group (including isomers), a dibutylphenyl group (including isomers), a dipentylphenyl group (including isomers), a dihexylphenyl group (including isomers), a diheptylphenyl group (including isomers), a terphenyl group (including isomers), a trimethylphenyl group (including isomers), a triethylphenyl group (including isomers), a tripropylphenyl group (including isomers) or a tributylphenyl group (including isomers); substituted or unsubstituted aryloxy groups such as a phenoxy group, a methylphenoxy group (including isomers), an ethylphenoxy group (including isomers), a propylphenoxy group (including isomers), a butylphenoxy group (including isomers), a pentylphenoxy group (including isomers), a hexylphenoxy group (including isomers), a heptylphenoxy group (including isomers), an octylphenoxy group (including isomers), a nonylphenoxy group (including isomers), a decylphenoxy group (including isomers), a phenylphenoxy group (including isomers), a dimethylphenoxy group (including isomers), a diethylphenoxy group (including isomers), a dipropylphenoxy group (including isomers), a dibutylphenoxy group (including isomers), a dipentylphenoxy group (including isomers), a dihexylphenoxy group (including isomers), a diheptylphenoxy group (including isomers), a diphenylphenoxy group (including isomers), a trimethylphenoxy group (including isomers), a triethylphenoxy group (including isomers), a tripropylphenoxy group (including isomers) or a tributylphenoxy group (including isomers); aralkyl groups such as a phenylmethyl group, a phenylethyl group (including isomers), a phenylpropyl group (including isomers), a phenylbutyl group (including isomers), a phenylpentyl group (including isomers), a phenylhexyl group (including isomers), a phenylheptyl group (including isomers), a phenyloctyl group (including isomers) or a phenylnonyl group (including isomers); and, aralkyloxy groups such as a phenylmethoxy group, a phenylethoxy group (including isomers), a phenylpropyloxy group (including isomers), a phenylbutyloxy group (including isomers), a phenylpentyloxy group (including isomers), a phenylhexyloxy group (including isomers), a phenylheptyloxy group (including isomers), a phenyloctyloxy group (including isomers) or a phenylnonyloxy group (including isomers).

Among these aromatic hydroxy compounds, aromatic hydroxy compounds in which at least one $R_1$ and $R_2$ and R are hydrogen atoms are used preferably. In this regard, R and at least one of $R_1$ and $R_2$ is selected from hydrogen and in another aspect all are selected to be hydrogen.

Preferable examples of aromatic hydroxy compounds represented by the formula above may include: phenol, methylphenol (including isomers), ethylphenol (including isomers), propylphenol (including isomers), butylphenol (including isomers), pentylphenol (including isomers), hexylphenol (including isomers), heptylphenol (including isomers), octylphenol (including isomers), nonylphenol (including isomers), decylphenol (including isomers), dodecylphenol (including isomers), octadecylphenol (including isomers), dimethylphenol (including isomers), diethylphenol (including isomers), dipropylphenol (including isomers), dibutylphenol (including isomers), dipentylphenol (including isomers), dihexylphenol (including isomers), diheptylphenol (including isomers), dioctylphenol (including isomers), dinonylphenol (including isomers), didecylphenol (including isomers), didodecylphenol (including isomers), dioctadecylphenol (including isomers), trimethylphenol (including isomers), triethylphenol (including isomers), tripropylphenol (including isomers), tributylphenol (including isomers), tripentylphenol (including isomers), trihexylphenol (including isomers), triheptylphenol (including isomers), trioctylphenol (including isomers), trinonylphenol (including isomers), tridecylphenol (including isomers), tridodecylphenol (including isomers), trioctadecylphenol (including isomers), (methoxymethyl)phenol (including isomers), (ethoxymethyl)phenol (including isomers), (propoxymethyl)phenol (including isomers), (butyloxymethyl)phenol (including isomers), (pentyloxymethyl)phenol (including isomers), (hexyloxymethyl)phenol (including isomers), (heptyloxymethyl)phenol (including isomers), (octyloxymethyl)phenol (including isomers), (nonyloxymethyl)phenol (including isomers), (decyloxymethyl)phenol (including isomers), (dodecyloxymethyl)phenol (including isomers), (octadecyloxymethyl)phenol (including isomers), (cyclopentyloxymethyl)phenol (including isomers), (cyclohexyloxymethyl)phenol (including isomers), (cycloheptyloxymethyl)phenol (including isomers), (cyclooctyloxymethyl)phenol (including isomers), (methylcyclopentyloxymethyl)phenol (including isomers), (ethylcyclopentyloxymethyl)phenol (including isomers), (methylcyclohexyloxymethyl)phenol (including isomers), (ethylcyclohexyloxymethyl)phenol (including isomers), (propylcyclohexyloxymethyl)phenol (including isomers), (butylcyclohexyloxymethyl)phenol (including isomers), (pentylcyclohexyloxymethyl)phenol (including isomers), (hexylcyclohexyloxymethyl)phenol (including isomers), (dimethylcyclohexyloxymethyl)phenol (including isomers), (diethylcyclohexyloxymethyl)phenol (including isomers), (dibutylcyclohexyloxymethyl)phenol (including isomers), (phenoxymethyl)phenol, (methylphenoxymethyl)phenol (including isomers), (ethylphenoxymethyl)phenol (including isomers), (propylphenoxymethyl)phenol (including isomers), (butylphenoxymethyl)phenol (including isomers), (pentylphenoxymethyl)phenol (including isomers), (hexylphenoxymethyl)phenol (including isomers), (heptylphenoxymethyl)phenol (including isomers), (octylphenoxymethyl)phenol (including isomers), (nonylphenoxymethyl)phenol (including isomers), (decylphenoxymethyl)phenol (including isomers), (phenylphenoxymethyl)phenol (including isomers), (dimethylphenoxymethyl)phenol (including isomers), (diethylphenoxymethyl)phenol (including isomers), (dipropylphenoxymethyl)phenol (including isomers), (dibutylphenoxymethyl)phenol (including isomers), (dipentylphenoxymethyl)phenol (including isomers), (dihexylphenoxymethyl)phenol (including isomers), (diheptylphenoxymethyl)phenol (including isomers), (diphenylphenoxymethyl)phenol (including isomers), (trimethylphenoxymethyl)phenol (including isomers), (triethylphenoxymethyl)phenol (including isomers), (tripropylphenoxymethyl)phenol (including isomers), (tributylphenoxymethyl)phenol (including isomers), (phenylmethoxymethyl)phenol (including isomers), (phenylethoxymethyl)phenol (including isomers), (phenylpropyloxymethyl)phenol (including isomers), (phenylbutyloxymethyl)phenol (including isomers), (phenylpentyloxymethyl)phenol (including isomers), (phenylhexyloxymethyl)phenol (including isomers), (phenylheptyloxymethyl)phenol (including isomers), (phenyloctyloxymethyl)phenol (including isomers), (phenylnonyloxymethyl)phenol (including isomers), di(methoxymethyl)phenol, di(ethoxymethyl)phenol, di(propoxymethyl)phenol (including isomers), di(butyloxymethyl)phenol (including isomers), di(pentyloxymethyl)phenol (including isomers), di(hexyloxymethyl)phenol (including isomers), di(heptyloxymethyl)phenol (including isomers), di(octyloxymethyl)phenol (including isomers), di(nonyloxymethyl)phenol (including isomers), di(decyloxymethyl)phenol (including isomers), di(dodecyloxymethyl)phenol (including isomers), di(octadecyloxymethyl)phenol (including isomers), di(cyclopentyloxymethyl)phenol (including isomers), di(cyclohexyloxymethyl)phenol (including isomers), di(cycloheptyloxymethyl)phenol (including isomers), di(cyclooctyloxymethyl)phenol (including isomers), di(methylcyclopentyloxymethy)phenol (including isomers), di(ethylcyclopentyloxymethyl)phenol (including isomers), di(methylcyclohexyloxymethyl)phenol (including isomers), di(ethylcyclohexyloxymethyl)phenol (including isomers), di(propylcyclohexyloxymethyl)phenol (including isomers), di(butylcyclohexyloxymethyl)phenol (including isomers), di(pentylcyclohexyloxymethyl)phenol (including isomers), di(hexylcyclohexyloxymethyl)phenol (including isomers), bis(dimethylcyclohexyloxymethyl)phenol (including isomers), bis(diethylcyclohexyloxymethyl)phenol (including isomers), bis(dibutylcyclohexyloxymethyl)phenol (including isomers), di(phenoxymethyl)phenol, di(methylphenoxymethyl)phenol (including isomers), di(ethylphenoxymethyl)phenol (including isomers), di(propylphenoxymethyl)phenol (including isomers), di(butylphenoxymethyl)phenol (including isomers), di(pentylphenoxymethyl)phenol (including isomers), di(hexylphenoxymethyl)phenol (including isomers), di(heptylphenoxymethyl)phenol (including isomers), di(octylphenoxymethyl)phenol (including isomers), di(nonylphenoxymethyl)phenol (including isomers), di(decylphenoxymethyl)phenol (including isomers), di(phenylphenoxymethyl)phenol (including isomers), bis(dimethylphenoxymethyl)phenol (including isomers), bis(diethylphenoxymethyl)phenol (including isomers), bis(dipropylphenoxymethyl)phenol (including isomers), bis(dibutylphenoxymethyl)phenol (including isomers), bis(dipentylphenoxymethyl)phenol (including isomers), bis(dihexylphenoxymethyl)phenol (including isomers), bis(diheptylphenoxymethyl)phenol (including isomers), bis(diphenylphenoxymethyl)phenol (including isomers), di(trimethylphenoxymethyl)phenol (including isomers), di(triethylphenoxymethyl)phenol (including isomers), di(tripropylphenoxymethyl)phenol (including isomers), di(tributylphenoxymethyl)phenol (including isomers), di(phenylmethoxymethyl)phenol (including isomers), di(phenylethoxymethyl)phenol (including isomers), di(phenylpropyloxymethyl)phenol (including isomers), di(phenylbutyloxymethyl)phenol (including isomers), di(phenylpentyloxymethyl)phenol (including isomers), di(phenylhexyloxymethyl)phenol (including isomers), di(phenylheptyloxymethyl)phenol (including isomers), di(phenyloctyloxymethyl)phenol (including isomers), di(phenylnonyloxymethyl)phenol (including isomers), tri(methoxymethyl)phenol, tri(ethoxymethyl)phenol, tri(propoxymethyl)phenol (including isomers), tri(butyloxymethyl)phenol (including isomers), tri(pentyloxymethyl)phenol (including isomers), tri(hexyloxymethyl)phenol (including isomers), tri(heptyloxymethyl)phenol (including isomers), tri(octyloxymethyl)phenol (including isomers), tri(nonyloxymethyl)phenol (including isomers), tri(decyloxymethyl)phenol (including isomers), tri(dodecyloxymethyl)phenol (including isomers), tri(octadecyloxymethyl)phenol (including isomers), tri(cyclopentyloxymethyl)phenol (including isomers), tri(cyclohexyloxymethyl)phenol (including isomers), tri(cycloheptyloxymethyl)phenol (including isomers), tri(cyclooctyloxymethyl)phenol (including isomers), tri(methylcyclopentyloxymethy)phenol (including isomers), tri(ethylcyclopentyloxymethyl)phenol (including isomers), tri(methylcyclohexyloxymethyl)phenol (including isomers), tri(ethylcyclohexyloxymethyl)phenol (including isomers), tri(propylcyclohexyloxymethyl)phenol (including isomers), tri(butylcyclohexyloxymethyl)phenol (including isomers), tri(pentylcyclohexyloxymethyl)phenol (including isomers), tri(hexylcyclohexyloxymethyl)phenol (including isomers), bis(dimethylcyclohexyloxymethyl)phenol (including isomers), bis(diethylcyclohexyloxymethyl)phenol (including isomers), bis(dibutylcyclohexyloxymethyl)phenol (including isomers), tri(phenoxymethyl)phenol, tri(methylphenoxymethyl)phenol (including isomers), tri(ethylphenoxymethyl)phenol (including isomers), tri(propylphenoxymethyl)phenol (including isomers), tri(butylphenoxymethyl)phenol (including isomers), tri(pentylphenoxymethyl)phenol (including isomers), tri(hexylphenoxymethyl)phenol (including isomers), tri(heptylphenoxymethyl)phenol (including isomers), tri(octylphenoxymethyl)phenol (including isomers), tri(nonylphenoxymethyl)phenol (including isomers), tri(decylphenoxymethyl)phenol (including isomers), tri(phenylphenoxymethyl)phenol (including isomers), bis(dimethylphenoxymethyl)phenol (including isomers), bis(diethylphenoxymethyl)phenol (including isomers), bis(dipropylphenoxymethyl)phenol (including isomers), bis(dibutylphenoxymethyl)phenol (including isomers), bis(dipentylphenoxymethyl)phenol (including isomers), bis(dihexylphenoxymethyl)phenol (including isomers), bis(diheptylphenoxymethyl)phenol (including isomers), bis(diphenylphenoxymethyl)phenol (including isomers), tri(trimethylphenoxymethyl)phenol (including isomers), tri(triethylphenoxymethyl)phenol (including isomers), tri(tripropylphenoxymethyl)phenol (including isomers), tri(tributylphenoxymethyl)phenol (including isomers), tri(phenylmethoxymethyl)phenol, tri(phenylethoxymethyl)phenol (including isomers), tri(phenylpropyloxymethyl)phenol (including isomers), tri(phenylbutyloxymethyl)phenol (including isomers), tri(phenylpentyloxymethyl)phenol (including isomers), tri(phenylhexyloxymethyl)phenol (including isomers), tri(phenylheptyloxymethyl)phenol (including isomers), tri(phenyloctyloxymethyl)phenol (including isomers), tri(phenylnonyloxymethyl)phenol (including isomers), (phenylmethyl)phenol (including isomers), ((methylphenyl)methyl)phenol (including isomers), ((ethylphenyl)methyl)phenol (including isomers), ((propylphenyl)methyl)phenol (including isomers), ((butylphenyl)methyl)phenol (including isomers), ((pentylphenyl)methyl)phenol (including isomers), ((hexylphenyl)methyl)phenol (including isomers), ((heptylphenyl)methyl)phenol (including isomers), ((octylphenyl)methyl)phenol (including isomers), ((nonylphenyl)methyl)phenol (including isomers), ((decylphenyl)methyl)phenol (including isomers), ((biphenyl)methyl)phenol (including isomers), ((dimethylphenyl)methyl)phenol (including isomers), ((diethylphenyl)methyl)phenol (including isomers), ((dipropylphenyl)methyl)phenol (including isomers), ((dibutylphenyl)methyl)phenol (including isomers), ((dipentylphenyl)methyl)phenol (including isomers), ((dihexylphenyl)methyl)phenol (including isomers), ((diheptylphenyl)methyl)phenol (including isomers), ((terphenyl)methyl)phenol (including isomers), ((trimethylphenyl)methyl)phenol (including isomers), ((triethylphenyl)methyl)phenol (including isomers), ((tripropylphenyl)methyl)phenol (including isomers), ((tributylphenyl)methyl)phenol (including isomers), di(phenylmethyl)phenol (including isomers), di((methylphenyl)methyl)phenol (including isomers), di((ethylphenyl)methyl)phenol (including isomers), di((propylphenyl)methyl)phenol (including isomers), di((butylphenyl)methyl)phenol (including isomers), di((pentylphenyl)methyl)phenol (including isomers), di((hexylphenyl)methyl)phenol (including isomers), di((heptylphenyl)methyl)phenol (including isomers), di((octylphenyl)methyl)phenol (including isomers), di((nonylphenyl)methyl)phenol (including isomers), di((decylphenyl)methyl)phenol (including isomers), di((biphenyl)methyl)phenol (including isomers), di((dimethylphenyl)methyl)phenol (including isomers), di((diethylphenyl)methyl)phenol (including isomers), di((dipropylphenyl)methyl)phenol (including isomers), di((dibutylphenyl)methyl)phenol (including isomers), di((dipentylphenyl)methyl)phenol (including isomers), di((dihexylphenyl)methyl)phenol (including isomers), di((diheptylphenyl)methyl)phenol (including isomers), di((terphenyl)methyl)phenol (including isomers), di((trimethylphenyl)methyl)phenol (including isomers), di((triethylphenyl)methyl)phenol (including isomers), di((tripropylphenyl)methyl)phenol (including isomers), di((tributylphenyl)methyl)phenol (including isomers), tri(phenylmethyl)phenol (including isomers), tri((methylphenyl)methyl)phenol (including isomers), tri((ethylphenyl)methyl)phenol (including isomers), tri((propylphenyl)methyl)phenol (including isomers), tri((butylphenyl)methyl)phenol (including isomers), tri((pentylphenyl)methyl)phenol (including isomers), tri((hexylphenyl)methyl)phenol (including isomers), tri((heptylphenyl)methyl)phenol (including isomers), tri((octylphenyl)methyl)phenol (including isomers), tri((nonylphenyl)methyl)phenol (including isomers), tri((decylphenyl)methyl)phenol (including isomers), tri((biphenyl)methyl)phenol (including isomers), tri((dimethylphenyl)methyl)phenol (including isomers), tri((diethylphenyl)methyl)phenol (including isomers), tri((dipropylphenyl)methyl)phenol (including isomers), tri((dibutylphenyl)methyl)phenol (including isomers), tri((dipentylphenyl)methyl)phenol (including isomers), tri((dihexylphenyl)methyl)phenol (including isomers), tri((diheptylphenyl)methyl)phenol (including isomers), tri((terphenyl)methyl)phenol (including isomers), tri((trimethylphenyl)methyl)phenol (including isomers), tri((triethylphenyl)methyl)phenol (including isomers), tri((tripropylphenyl)methyl)phenol (including isomers), tri((tributylphenyl)methyl)phenol (including isomers), phenylethylphenol (including isomers), phenyl-n-propylphenol (including isomers), phenyl-n-butylphenol (including isomers), phenyl-n-pentylphenol (including isomers), phenyl-n-hexylphenol (including isomers), phenyl-n-heptylphenol (including isomers), phenyl-n-octylphenol (including isomers), phenyl-n-nonylphenol (including isomers), methoxyphenol (including isomers), ethoxyphenol (including isomers), propyloxyphenol (including isomers), butyloxyphenol (including isomers), pentyloxyphenol (including isomers), hexyloxyphenol (including isomers), heptyloxyphenol (including isomers), octyloxyphenol (including isomers), nonyloxyphenol (including isomers), decyloxyphenol (including isomers), dodecyloxyphenol (including isomers), octadecyloxyphenol (including isomers), cyclopentyloxyphenol (including isomers), cyclohexyloxyphenol (including isomers), cycloheptyloxyphenol (including isomers), cyclooctyloxyphenol (including isomers), (methylcyclopentyloxy)phenol (including isomers), (ethylcyclopentyloxy)phenol (including isomers), (methylcyclohexyloxy)phenol (including isomers), (ethylcyclohexyloxy)phenol (including isomers), (propylcyclohexyloxy)phenol (including isomers), (butylcyclohexyloxy)phenol (including isomers), (pentylcyclohexyloxy)phenol (including isomers), (hexylcyclohexyloxy)phenol (including isomers), (dimethylcyclohexyloxy)

phenol (including isomers), (diethylcyclohexyloxy)phenol (including isomers), (dibutylcyclohexyloxy)phenol (including isomers), phenoxyphenol, (methylphenyloxy)phenol (including isomers), (ethylphenyloxy)phenol (including isomers), (propylphenyloxy)phenol (including isomers), (butylphenyloxy)phenol (including isomers), (pentylphenyloxy)phenol (including isomers), (hexylphenyloxy)phenol (including isomers), (heptylphenyloxy)phenol (including isomers), (octylphenyloxy)phenol (including isomers), (nonylphenyloxy)phenol (including isomers), (decylphenyloxy)phenol (including isomers), biphenyloxyphenol (including isomers), (dimethylphenyloxy)phenol (including isomers), (diethylphenyloxy)phenol (including isomers), (dipropylphenyloxy)phenol (including isomers), (dibutylphenyloxy)phenol (including isomers), (dipentylphenyloxy)phenol (including isomers), (dihexylphenyloxy)phenol (including isomers), (diheptylphenyloxy)phenol (including isomers), terphenyloxyphenol (including isomers), (trimethylphenyloxy)phenol (including isomers), (triethylphenyloxy)phenol (including isomers), (tripropylphenyloxy)phenol (including isomers), (tributylphenyloxy)phenol (including isomers), (phenylmethyloxy)phenol, (phenylethyloxy)phenol (including isomers), (phenylpropyloxy)phenol (including isomers), (phenylbutyloxy)phenol (including isomers), (phenylpentyloxy)phenol (including isomers), (phenylhexyloxy)phenol (including isomers), (phenylheptyloxy)phenol (including isomers), (phenyloctyloxy)phenol (including isomers), (phenylnonyloxy)phenol (including isomers), dimethoxyphenol (including isomers), diethoxyphenol (including isomers), dipropyloxyphenol (including isomers), dibutyloxyphenol (including isomers), dipentyloxyphenol (including isomers), dihexyloxyphenol (including isomers), diheptyloxyphenol (including isomers), dioctyloxyphenol (including isomers), dinonyloxyphenol (including isomers), didecyloxyphenol (including isomers), didodecyloxyphenol (including isomers), dioctadecyloxyphenol (including isomers), dicyclopentyloxyphenol (including isomers), dicyclohexyloxyphenol (including isomers), dicycloheptyloxyphenol (including isomers), dicyclooctyloxyphenol (including isomers), di(methylcyclopentyloxy)phenol (including isomers), di(ethylcyclopentyloxy)phenol (including isomers), di(methylcyclohexyloxy)phenol (including isomers), di(ethylcyclohexyloxy)phenol (including isomers), di(propylcyclohexyloxy)phenol (including isomers), di(butylcyclohexyloxy)phenol (including isomers), di(pentylcyclohexyloxy)phenol (including isomers), di(hexylcyclohexyloxy)phenol (including isomers), bis(dimethylcyclohexyloxy)phenol (including isomers), bis(diethylcyclohexyloxy)phenol (including isomers), bis(dibutylcyclohexyloxy)phenol (including isomers), phenyloxyphenol, di(methylphenyloxy)phenol (including isomers), di(ethylphenyloxy)phenol (including isomers), di(propylphenyloxy)phenol (including isomers), di(butylphenyloxy)phenol (including isomers), di(pentylphenyloxy)phenol (including isomers), di(hexylphenyloxy)phenol (including isomers), di(heptylphenyloxy)phenol (including isomers), di(octylphenyloxy)phenol (including isomers), di(nonylphenyloxy)phenol (including isomers), di(decylphenyloxy)phenol (including isomers), dibiphenyloxyphenol (including isomers), bis(dimethylphenyloxy)phenol (including isomers), bis(diethylphenyloxy)phenol (including isomers), bis(dipropylphenyloxy)phenol (including isomers), bis(dibutylphenyloxy)phenol (including isomers), bis(dipentylphenyloxy)phenol (including isomers), bis(dihexylphenyloxy)phenol (including isomers), bis(diheptylphenyloxy)phenol (including isomers), diterphenyloxyphenol (including isomers), di(trimethylphenyloxy)phenol (including isomers), di(triethylphenyloxy)phenol (including isomers), di(tripropylphenyloxy)phenol (including isomers), di(tributylphenyloxy)phenol (including isomers), di(phenylmethyloxy)phenol, di(phenylethyloxy)phenol (including isomers), di(phenylpropyloxy)phenol (including isomers), di(phenylbutyloxy)phenol (including isomers), di(phenylpentyloxy)phenol (including isomers), di(phenylhexyloxy)phenol (including isomers), di(phenylheptyloxy)phenol (including isomers), di(phenyloctyloxy)phenol (including isomers), di(phenylnonyloxy)phenol (including isomers), trimethoxyphenol (including isomers), triethoxyphenol (including isomers), tripropyloxyphenol (including isomers), tributyloxyphenol (including isomers), tripentyloxyphenol (including isomers), trihexyloxyphenol (including isomers), triheptyloxyphenol (including isomers), trioctyloxyphenol (including isomers), trinonyloxyphenol (including isomers), tridecyloxyphenol (including isomers), tridodecyloxyphenol (including isomers), trioctadecyloxyphenol (including isomers), tricyclopentyloxyphenol (including isomers), tricyclohexyloxyphenol (including isomers), tricycloheptyloxyphenol (including isomers), tricyclooctyloxyphenol (including isomers), tri(methylcyclopentyloxy)phenol (including isomers), tri(ethylcyclopentyloxy)phenol (including isomers), tri(methylcyclohexyloxy)phenol (including isomers), tri(ethylcyclohexyloxy)phenol (including isomers), tri(propylcyclohexyloxy)phenol (including isomers), tri(butylcyclohexyloxy)phenol (including isomers), tri(pentylcyclohexyloxy)phenol (including isomers), tri(hexylcyclohexyloxy)phenol (including isomers), tri(dimethylcyclohexyloxy)phenol (including isomers), tri(diethylcyclohexyloxy)phenol (including isomers), tri(dibutylcyclohexyloxy)phenol (including isomers), phenyloxyphenol, tri(methylphenyloxy)phenol (including isomers), tri(ethylphenyloxy)phenol (including isomers), tri(propylphenyloxy)phenol (including isomers), tri(butylphenyloxy)phenol (including isomers), tri(pentylphenyloxy)phenol (including isomers), tri(hexylphenyloxy)phenol (including isomers), tri(heptylphenyloxy)phenol (including isomers), tri(octylphenyloxy)phenol (including isomers), tri(nonylphenyloxy)phenol (including isomers), tri(decylphenyloxy)phenol (including isomers), tribiphenyloxyphenol (including isomers), tri(dimethylphenyloxy)phenol (including isomers), tri(diethylphenyloxy)phenol (including isomers), tri(dipropylphenyloxy)phenol (including isomers), tri(dibutylphenyloxy)phenol (including isomers), tri(dipentylphenyloxy)phenol (including isomers), tri(dihexylphenyloxy)phenol (including isomers), tri(diheptylphenyloxy)phenol (including isomers), triterphenyloxyphenol (including isomers), tri(trimethylphenyloxy)phenol (including isomers), tri(triethylphenyloxy)phenol (including isomers), tri(tripropylphenyloxy)phenol (including isomers), tri(tributylphenyloxy)phenol (including isomers), tri(phenylmethyloxy)phenol, tri(phenylethyloxy)phenol (including isomers), tri(phenylpropyloxy)phenol (including isomers), tri(phenylbutyloxy)phenol (including isomers), tri(phenylpentyloxy)phenol (including isomers), tri(phenylhexyloxy)phenol (including isomers), tri(phenylheptyloxy)phenol (including isomers), tri(phenyloctyloxy)phenol (including isomers), tri(phenylnonyloxy)phenol (including isomers), phenylphenol (including isomers), and naphthol (including isomers). In another aspect, the phenol base aromatic moiety above may be replaced with naphthol base aromatic moiety, in each instance, for the sake of brevity such substituted naphthols are incorporated herein.

In this regard, particularly suited aromatic hydroxyl compounds are selected from phenol and substituted phenols have 1 to 2 substituent's selected from alkyl having 1 to 12 carbon atoms, aryl, arylalkyl, alkylaryl, aryloxy having 7 to 24 carbon atoms; naphthol and substituted naphthols have 1 to 2 substituent's selected from alkyl having 1 to 12 carbon atoms, aryl, arylalkyl, alkylaryl, aryloxy having 7 to 24 carbon atoms, in another aspect the substituted phenol may be acylaromatic such as hydroxybenzophenone and the like.

The aminoethylation reaction of an aromatic hydroxyl compound is conducted in the presence of a basic catalyst with a 2-oxazolidinone of the formula II:

Formula II

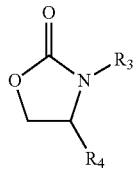

wherein $R_3$ is selected from the group consisting of hydrogen or lower alkyl having 1 to 6 carbon atoms, $R_4$ is selected from the group consisting of hydrogen, straight or branched chain alkyl having from one to six carbon atoms, phenyl, alkaryl, or arylalkyl. Preferable alkaryl and arylalkyl are selected from 7 to 16 carbon atoms and wherein the aryl group is benzene.

Examples of suitable oxazolidinone compounds include, but are not limited to, 2-oxazolidinone, 4-methyl-2-oxazolidinone, 4-isopropyl-2-oxazolidinone, 4-phenyl-2-oxazolidinone, and 4-benzyl-2-oxazolidinone. The 2-oxazolidinone compound is preferred. These compounds are readily commercially available and may be purchased for example from Sigma-Aldrich Chemical Company. Alternatively, these compounds may be synthesized by conventional methods apparent to the skilled artisan.

Alternatively, the oxazolidinone compound may be produced in-situ by reacting a β-amino alcohol with a dialkyl carbonate. Suitable β-amino alcohols are of the formula $NH_2$—$CHR_{10}CH_2$—OH wherein $R_{10}$ is a lower alkyl having 1 to 6 carbon atoms, phenyl, alkylaryl, or arylalkyl and the dialkyl carbonate is of the formula $(R_{11}O)_2CO$ where $R_{11}$ is lower alkyl having 1 to about 6 carbon atoms. In this regard the β-amino alcohol and the dialkyl carbonate may react to form carbamate intermediates and 2-oxazolidinones which further react. In another aspect α-aminoacids may be employed likewise from β-amino alcohols and/or in-situ formation of the 2-oxaxolidinone. When the 2-oxazolidinone is prepared in-situ, typically the molar ratio of the β-amino alcohol and dialkyl carbonate to the aromatic hydroxyl compound is normally in the range of about equi-parts (β-amino alcohol and dialkyl carbonate) to 5:1 to 0.9:1 to the aromatic hydroxyl compound, and preferably will be in the range of about 2:1 to 1:1. In general, the number of equivalents of the basic catalyst per equivalents of aromatic hydroxyl compound will be in the range of about 0.05:1 to 1:1, and preferably in the range of about 0.1:1 to 1:1.

The basic catalyst employed in the process of the present invention will generally be any of the well known basic catalysts selected from the group of alkali metal lower alkoxides, alkali hydrides or alkali metal hydroxides. Typical alkali metal lower alkoxides include, but are not limited to, sodium methoxide, potassium methoxide, sodium ethoxide, potassium ethoxide, sodium propoxide, potassium propoxide, sodium isopropoxide, potassium isopropoxide, sodium butoxide, potassium butoxide. Typically, the alkali metal lower alkoxides will contain 1 to about 6, preferably 1 to about 4, carbon atoms. Preferably, the alkali metal lower alkoxide is sodium methoxide. Sodium hydride and potassium hydride are typical alkali hydrides. Examples of alkali metal hydroxides include, but are not limited to, sodium hydroxide, lithium hydroxide, or potassium hydroxide. Sodium hydroxide and potassium hydroxide are preferred.

Typically, the reaction temperature for the aminoethylation reaction will be in the range of about 100° C. to 250° C., and preferably in the range of about 130° C. to 210° C. The reaction pressure will generally be atmospheric or lower. Lower pressures may be used to facilitate the removal of carbon dioxide. Other carbon dioxide scavengers may be employed to facilitate the reaction, such as, for example, magnesium oxide or calcium oxide.

The molar ratio of 2-oxazolidinone or a derivative thereof to the aromatic hydroxyl compound is normally in the range of about 5:1 to 0.9:1, and preferably will be in the range of about 2:1 to 1:1 and more preferable in excess such as 1.2:1 and greater. In general, the number of equivalents of the basic catalyst per equivalents of aromatic hydroxyl compound will be in the range of about 0.05:1 to 1:1, and preferably in the range of about 0.1:1 to 1:1.

The aminoethylation reaction may be carried out neat or in the presence of a solvent which is inert to the reaction of the aromatic hydroxyl compound and the 2-oxazolidinone or a derivative thereof. An inert solvent is often used to facilitate handling and to promote good contacting of the reactants. When employed, examples of inert solvents include heptane, benzene, toluene, chlorobenzene and 250 thinner which is a mixture of aromatics, paraffin's and naphthenes. Kerosene-type jet fuel is another example of the latter mixture. Other examples of inert solvents that are aromatic mixtures include Exxon Aromatic 100, Exxon Aromatic 150, Solvesso 100, Total Solvarex 9 and the like. Other solvents apparent to those skilled in the art may also be used. For example, any number of ethers, aprotic polar solvents or alcohols may also be useful in the process of the present invention. Particularly suited alcohols are alkylalcohols. Examples of typical alcohols include n-propanol, n-butanol, 1-pentanol, 1-hexanol, 1-heptanol, and mixed isomers of each of the foregoing alcohols including branched- or straight-chain alcohols.

1-Hexanol or hexanol isomers are preferred. Examples of commercial alcohols available from ExxonMobil Chemical that are a mix of several isomers include Exxal 6 (hexyl alcohol) and Exxal 7 (isoheptyl alcohol).

The aminoethylation intermediate reaction product mixture will thereafter be reacted with an alkylene polyamine to thereby react at least a portion of the N,N'-bis(aryloxyalkylene)urea reaction by-product to the desired aryloxy-alkylene amine product. The molar ratio of alkylene polyamine to aromatic hydroxyl compound is normally in the range of 0.1:1 to 1.0:1, preferably in the range of 0.5:1 to 0.7:1. In another embodiment, an equimolar amount of alkylene polyamine relative to the amount of dialkylene urea that is formed in the reaction is used. The amount of dialkylene urea can be determined by analytical tools know to those skilled in the art. The reaction is conducted at a temperature of 100 to 200° C., more preferably in the range of 140 to 180° C. The reaction progress may be monitored for the substantially complete conversion of the dialkylene urea to the aryloxy-alkylene amine.

Suitable alkylene polyamines are typically of the formula

wherein x is an integer of from about 0 to 10, A is an alkylene radical of from 2 to 10, preferably from about 2 to 3 carbon atoms, $R_5$, $R_6$ and $R_7$ are independently selected from hydrogen, an alkyl from 1 to 6 carbon atoms group. Suitable A groups are ethylene, 1,2 propylene, 2,2-dimethylpropylene, etc. Particularly well suited alkylene polyamines include those containing 1,2-diamine and 1,3-diamine functionality wherein the diamine has a primary or secondary amine function.

The alkylene polyamines include principally derived from methylene amines, ethylene amines, butylene amines, propylene amines, pentylene amines, hexylene amines, heptylene amines, octylene amines, other polymethylene amines and also may include a small amount of the cyclic and the higher homologs of such amines as piperazine and amino alkyl-substituted piperazines. They are exemplified specifically by ethylene diamine, diethylene triamine, triethylene tetraamine, tetraethylene pentamine, propylene diamine, decamethyl diamine, octamethylene diamine, diheptamethylene triamine, tripropylene tetraamine, trimethylene diamine, pentaethylene hexamine, ditrimethylene triamine and the like. Heavy polyamine, such as HPA-X sold by the Dow Chemical company, can also be useful. Higher homologs such as are obtained by condensing two or more of the above-illustrated alkylene amines likewise are useful.

The ethylene amines are especially useful. They are described in some detail under the heading "Ethylene Amines" in Encyclopedia of Chemical Technology, Kirk-Othmer, Vol. 5, pp. 898-905 (Interscience Publishers, New York, 1950).

The term "ethylene amine" is used in a generic sense to denote a class of polyamines conforming for the most part to the structure $H_2N(CH_2CH_2NH)_aH$ wherein a is an integer from 1 to 10, preferably 1 to 4.

Thus, it includes, for example, ethylene diamine, diethylene triamine, triethylene tetraamine, tetraethylene pentamine, pentaethylene hexamine, and the like. Most preferred are ethylene diamine and diethylene triamine, particularly ethylene diamine.

The aminoethylation reaction will generally be carried out over a period of about 2 to 24 hours, and preferably over a period of about 3 to 20 hours. Upon completion of the reaction, the desired aryloxyalkylene amine is isolated using conventional techniques.

EXAMPLES

The invention will be further illustrated by the following examples, which set forth particularly advantageous process embodiments. While the Examples are provided to illustrate the present invention, they are not intended to limit it. This application is intended to cover those various changes and substitutions that may be made by those skilled in the art without departing from the spirit and scope of the appended claims.

Methods for preparing aryloxyethylene amines in high yield and purity.

Method 1: Use of Equimolar 2-Oxazolidinone Relative to Aromatic Hydroxyl Compound without Alkylene Polyamine Treatment—Comparative In a typical embodiment, when an aromatic hydroxyl compound is reacted with only a single equivalent of 2-oxazolidinone, the conversion of the aromatic hydroxyl compound is approximately 65-80% (see Table 1). Three major products are formed in the reaction including the aryloxyalkylene amine, N,N'-bis(aryloxyalkylene)urea, and imidazolidinone (see Products Scheme A).

Method 2: Use of Molar Excess of 2-Oxazolidinone Relative to Aromatic Hydroxyl Compound without Alkylene Polyamine Treatment—Comparative The use of a molar excess (~1.6 equivalents) of 2-oxazolidinone results in complete conversion of the aromatic hydroxyl compound to three major products. These products include the aryloxyalkylene amine, N,N'-bis(aryloxyalkylene)urea, and imidazolidinone (see Products Scheme A). The molar ratios observed in a typical reaction are found in Table 1 (note there are two moles of product consumed to make one mole N,N'-bis(aryloxyalkylene)urea).

TABLE 1

Conversion and product ratios using Methods 1 & 2.

| Equivalents 2-oxazolidinone | % conversion of 2-naphthol | aryloxyalkylene amine | N,N'-bis(aryloxyalkylene) urea | Imidazolidinone | Yield of Aryloxy-ethanamine |
|---|---|---|---|---|---|
| 1.0 (Method 1) | 65% | 1 | 0.2-0.4 | 0.05-0.1 | N.D. |
| 1.6 (Method 2) | 100% | 1 | 0.2-0.4 | 0.05-0.1 | 50-60% |

Method 3. Use of Molar Excess of Oxazolidinone Relative to Aromatic Hydroxyl Compound with In Situ Alkylene Polyamine Treatment In Method 3, the procedure of Method 2 is followed using 1.6 equivalents of 2-oxazolidinone to obtain complete conversion of the aromatic hydroxy compound into products. Following complete conversion, the alkylene polyamine is added directly to the reaction mixture and heating is continued until all of the dialkylene urea has been converted into the aryloxyalkylene amine. In this embodiment, the reaction yields only the desired aryloxyethanamine product along with small amounts of the imidazolidinone by-product. Reaction yields of the aryloxyethanamine are significantly improved relative to Method 2. Typical yields are 90-95% based on starting aromatic hydroxy compound (see Table 2).

TABLE 2

Conversion and product fractions using Method 3.

| Equivalents 2-oxazolidinone | % conversion of 2-naphthol | aryloxyalkylene amine | N,N'-bis(aryloxyalkylene) urea | Imidazolidinone | Yield of Aryloxy-ethanamine |
|---|---|---|---|---|---|
| 1.6 | 100% | 1 | 0.0 | 0.05-0.1 | 90-95% |

Method 4: Use of Ethanolamine and Diethylcarbonate for In-Situ 2-Oxazolidinone Formation.

In another embodiment, the reaction may be conducted using an equimolar amount of β-aminoalcohol and a dialkylcarbonate, such as ethanolamine and diethylcarbonate, in lieu of the direct addition of 2-oxazolidinone. These two reagents react in-situ to form 2-oxazolidinone, which then react with the aromatic hydroxy compound as in Method 2. When using 1.6 equivalents of both the ethanolamine and diethylcarbonate, the reaction outcome is identical to using Method 2 in terms of product ratios, conversion and yields. Addition of a suitable alkylene polyamine, such as ethylenediamine, to the reaction after the 2-naphthol has been converted to products leads to identical results as in Method 3.

Example 1

Preparation of 2-(2-naphthoxy)ethylamine using Method 2—Comparative

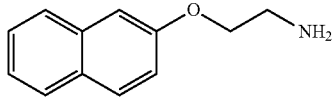 [SMILES: NCCOc1ccc2ccccc2c1]

A solution of 2-naphthol (50 g, 347 mmole), 2-oxazolidinone (48 g, 555 mmole), and potassium hydroxide (2.2 g, 34.7 mmole) in 100 mL ExxonMobil™ Aromatic 100 solvent was heated to reflux temperature (~170° C.) for four hours in a 350 mL flask equipped with a Dean-Stark trap, reflux condenser, and Nitrogen inlet and outlet. The reaction progress was monitored by TLC. After conversion of all the 2-naphthol, the reaction mixture was cooled to room temperature. $^1$H NMR analysis of the crude mixture showed a product:urea ratio of ~4:1. The solids were filtered to give 40.6 g (29%) of the dialkylene urea (N,N'-bis(2-(2-naphthoxy)ethyl)Urea). The filtrate was concentrated to give 31.8 g (49%) of the desired product (2-(2-naphthoxy)ethylamine) with a >90% purity as determined by NMR.

2-(2-naphthoxy)ethylamine: $^1$H NMR (DMSO-d6, 400 MHz) δ 7.85-7.79 (m, 3H), 7.50-7.44 (m, 1H), 7.38-7.33 (m, 1H), 7.31 (d, 1H, J=2.6 Hz), 7.23 (dd, 1H, J=9.0, 2.6 Hz), 4.04 (dd, 2H, J=5.7, 5.7 Hz), 3.99 (dd, 2H, J=5.7, 5.7 Hz), 1.74 (bs, 2H); $^{13}$C NMR (DMSO-d6, 400 MHz): 157.6, 135.3, 130.2, 129.4, 128.4, 127.6, 127.2, 124.4, 119.7, 107.6, 71.3, 42.0; MS (ESI) for $C_{12}H_{13}NO$ [M+H] calc. 187.24. found 187.66; IR (film): 3364, 3279, 3061, 2940, 2830, 1626, 1597, 1509, 1469, 1456, 1389, 1370, 1357, 1313, 1259, 1216, 1181, 1141, 1118, 1086, 1014.

N,N'-bis(2-(2-naphthoxy)ethyl)Urea: $^1$H NMR (DMSO-d6, 400 MHz) δ 7.84-7.56 (m, 3H), 7.44 (ddd, 1 H, J=7.0, 7.0, 1.3 Hz), 7.36-7.30 (m, 2H), 7.16 (dd, 1H, J=8.8, 2.5 Hz), 6.31 (dd, 1H, J=5.7, 5.7 Hz), 4.09 (dd, 1H, J=5.75 Hz), 3.46 (ddd, 1H, J=5.7, 5.7, 5.7 Hz); $^{13}$C NMR (DMSO-d6, 400 MHz) δ 159.0, 157.3, 135.2, 130.2, 129.4, 128.4, 127.6, 127.3, 124.5, 119.6, 107.7, 68.3: MS (ESI) for $C_{25}H_{24}N_2O_3$ [M+Na] calc. 423.46. found 423.04; IR (film): 3312, 3056, 2967, 2928, 1624, 1589, 1507, 1465, 1439, 1389, 1356, 1256, 1214, 1182, 1056, 1029.

Example 2

Conversion of N,N'-bis(2-(2-naphthoxy)ethyl)Urea to 2-(2-naphthoxy)ethylamine

To a solution of N,N'-bis(2-(2-naphthoxy)ethyl)Urea (8 g, 19.98 mmole) in 40 mL ExxonMobil™ Aromatic 100 was added ethylene diamine (4 mL, 59.9 mmole). The reaction mixture was heated to reflux temperature for 15 h. The solvents were evaporated to give 6.82 g of the crude reaction mixture containing 2-(2-naphthoxy)ethylamine and 2-imidazolidinone as the by-product. The crude material was dissolved in toluene, treated with Magnesol®, and filtered over a bed of Celite®. The solvent was evaporated under reduced pressure to give 5.65 g (76%) of 2-(2-naphthoxy)ethylamine which was spectroscopically identical to the product isolated in Example 1.

Example 3

Preparation of 2-(2-naphthoxy)ethylamine using Method 3

To a 3 L round bottom flask equipped with a thermocouple, heating mantle, nitrogen inlet/outlet, a condenser and a stir bar was added ExxonMobil™ Aromatic 100 solvent (1.4 L) and 2-naphthol (200 g, 1.39 mol) at room temperature. Potassium hydroxide pellets (8.99 g, 0.139 mol) and 2-oxazolidinone (181 g, 2.08 mol) were then added, and the reaction mixture was heated to reflux and stirred for 5.5 h. Reaction was monitored by TLC analysis. Additional 2-oxazolidinone (24.0 g, 0.277 mol) was added to ensure complete conversion of the 2-naphthol and the reaction mixture was heated to reflux temperature for 16 additional hours. The reaction mixture was cooled to 70° C. and ethylenediamine (18.5 mL, 0.277 mmole) was added. The reaction mixture was then reheated to reflux temperature (approximately 155° C.) under nitrogen and stirred for approximately 6 hours. The reaction mixture was cooled to room temperature and Magnesol® was added and stirred into the reaction mixture for 15 minutes. The reaction mixture was then filtered over Celite® and reaction flask was washed three times with ExxonMobil™ Aromatic 100 solvent. The filtrate was collected and the solvent was evaporated in vacuo to obtain 254.1 g (97%) of 2-(2-naphthoxy)ethylamine. Purity was determined by HPLC and NMR analysis to be ~92%.

Example 4

Preparation of 2-(2-naphthoxy)ethylamine from ethanolamine and diethylcarbonate using Method 4

To a 3-neck round bottom flask equipped with a Dean-Stark trap with a condenser, temperature probe, and mechanical stirrer at room temperature was added 2-naphthol (100 g, 0.694 mol). Potassium hydroxide pellets (3.89 g, 0.069 mol), ethanol amine (67.8 g, 1.110 mol), ExxonMobil™ Aromatic 100 solvent (693 mL) followed by diethyl carbonate (130.65 g, 1.110 mol) were then added, and the reaction mixture was heated to 118-120° C. and stirred for 1 h. The reaction temperature was then increased to 155° C. over 2 h, during which the distillates were being removed via the Dean-Stark trap. The reaction temperature was then set to 170° C. and held for 3 h. Reaction was monitored by NMR $^1$H analysis. Following complete conversion of the 2-naphthol, the reaction mixture was cooled to 70° C. and ethylene diamine (23.2 mL, 0.347 mmole) was added. The reaction mixture was then reheated to reflux (161° C.) under nitrogen and stirred for 2 hours. The reaction mixture was cooled to room temperature and Magnesol® was added and stirred into the reaction mixture for 15 minutes. The reaction mixture was then filtered over Celite® and reaction flask was washed three times with ExxonMobil™ Aromatic 100 solvent. The combined filtrates were collected and the solvent was evaporated in vacuo to obtain 127.25 g (98%, >88% purity by NMR 1H) of a dark amber liquid.

Example 5

Preparation of 2-phenoxyethylamine using Method 3

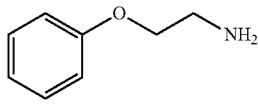

To a 250 mL round bottom flask equipped with a thermocouple, heating mantle, nitrogen inlet/outlet, a condenser and a stir bar was added 2-oxazolidinone (14.8 g, 170 mmole), phenol (10.0 g, 106.3 mmole), potassium hydroxide (596 mg, 10.6 mmole) and ExxonMobil™ Aromatic 100 solvent (100 mL). The resulting mixture was heated to reflux temperature for 3 h. Reaction progress was monitored by TLC and $^1$H NMR. Once the phenol was consumed, ethylenediamine (3.6 mL, 53 mmole) was added and the reaction mixture was continued to stir at reflux temperature for 2 hrs. The reaction mixture was then cooled to room temperature. Florisil® (5 g) was added and the reaction mixture was filtered over Celite. The reactor and the filter cake were washed with ExxonMobil™ Aromatic 100 solvent (2×10 mL). The combined filtrates were concentrated under reduced pressure to give 12.3 g (84%) of the desired product as a yellow oil. Purity level was determined by NMR to be ~95%. $^1$H NMR (CDCl$_3$, 400 MHz) δ 7.22-7.14 (m, 2H), 6.89-6.77 (m, 3H), 3.80 (dd, 2H, J=5.3, 5.3 Hz)), 2.90 (dd, 2H, J=5.4, 5.4 Hz), 1.41 (bs, 2H), $^{13}$C NMR (CDCl$_3$, 400 MHz) 158.9, 129.4, 120.7, 114.4, 70.0, 41.5, MS (ESI) for C$_8$H$_{11}$NO [M+H] calc. 137.08. found 137.56.

Example 6

Preparation of 2-(2-nonylphenoxy) using Method 3

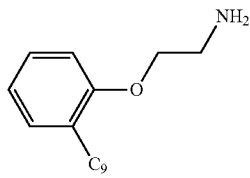

To a 250 mL round bottom flask equipped with a thermocouple, heating mantle, nitrogen inlet/outlet, a condenser and a stir bar was added 2-oxazolidinone (6.72 g, 77.2 mmole), 2-nonylphenol (10.0 g, 45.4 mmole (tech grade)), potassium hydroxide (255 mg, 4.5 mmole) and ExxonMobil™ Aromatic 100 solvent (70 mL). The resulting mixture was heated to reflux temperature for 3 h. Reaction progress was monitored by TLC and $^1$H NMR. The ratio of product to urea was determined to be ~2:1 by $^1$H NMR. Once the 2-nonylphenol was consumed, ethylenediamine (9.1 mL, 136 mmole) was added and the reaction mixture was continued to stir at reflux temperature for 5 hrs. The reaction mixture was then cooled to room temperature. The crude material was diluted with 100 mL ethyl acetate and washed twice with 100 mL water, then 100 ml brine. The organic layer was separated, dried over sodium sulfate and concentrated under reduced pressure to give 11.54 g (97% yield) of the desired amine as a yellow oil. Purity level was determined by NMR to be >95%. $^1$H NMR (DMSO-d6, 400 MHz) δ 7.26-7.12 (m, 2H), 6.88-6.81 (m, 2H), 3.87 (dd, 2H, J=5.8, 5.8 Hz), 2.86 (dd, 2H, J=5.8, 5.8 Hz), 1.75-0.42 (m, 19H).

Examples 7-9

Use of Different Alkylene Amines

To illustrate the use of other alkylene amines in this invention, several experiments were conducted using different readily available polyamines such as diethylenetriamine (DETA), triethylenetriamine (TETA) and heavy polyamine (HPA). The DETA and TETA worked very well in converting the N,N'-bis(aryloxyalkylene)urea by-product to the desired product in situ. These amines also required less reaction time due to the higher temperatures that could be achieved. For practical purposes, EDA is the preferred amine due to the ease of removal of the excess amine following the reaction. The use of HPA was illustrated as exemplified in Example 2 starting from the isolated dialkylene urea. Due to solubility issues with the aromatic solvent this reaction was conducted in the absence of solvent. Complete conversion of the N,N'-bis(aryloxyalkylene)urea was observed with a 77% isolated product yield.

Example 7

To a 100 mL round bottom flask equipped with a thermocouple, heating mantle, nitrogen inlet/outlet, a condenser and a stir bar was added 2-oxazolidinone (10.3 g, 117.9 mmole), 2-naphthol (10.0 g, 69.4 mmole), potassium hydroxide (389 mg, 6.9 mmole) and ExxonMobil™ Aromatic 100 solvent (35 mL). The resulting mixture was heated to reflux temperature for 18 h. Reaction progress was monitored by TLC and $^1$H NMR. A ~2:1 ratio of desired product to N,N'-bis(aryloxyalkylene)urea was observed by NMR. Once the 2-naphthol was consumed, diethylene triamine (7.5 mL, 69.4 mmole) was added and the reaction mixture was continued to stir at reflux temperature until all of the urea was consumed. After 1 hrs, the reaction mixture was then cooled to room temperature and charged with Florisil (2 g) and stirred for 10 min. then filtered over Celite. The reactor and the filter cake were washed with ExxonMobil™ Aromatic 100 solvent (2×10 mL). The combined filtrates were washed with water (2×100 ml) then the organic layer was concentrated under reduced pressure to give 11.2 g (86% yield) of the desired amine as an amber oil. Purity level was determined by NMR to be >90%.

Example 8

To a 250 mL round bottom flask equipped with a thermocouple, heating mantle, nitrogen inlet/outlet, a condenser and a stir bar was added 2-oxazolidinone (10.3 g, 117.9 mmole), 2-naphthol (10.0 g, 69.4 mmole), potassium hydroxide (389 mg, 6.9 mmole) and ExxonMobil™ Aromatic 100 solvent (35 mL). The resulting mixture was heated to reflux temperature for 3.5 h. Reaction progress was monitored by TLC and $^1$H NMR. A ~1:1 ratio of desired product to N,N'-bis(aryloxyalkylene)urea was observed. Once the 2-naphthol was consumed, triethylene tetramine (3.6 mL, 24.3 mmole) was added and the reaction mixture was continued to stir at reflux temperature until all of the urea was consumed. After 2 hr, the reaction mixture was then cooled to room temperature and charged with Florisil (2.5 g) and stirred for 10 min. during that time, the Celite began to gum up and the mixture stopped stirring. The solution was separated and the solids in the flask were triturated with ExxonMobil™ Aromatic 100 solvent (2×20 mL) then filtered over Celite. The solids remaining solids in the flask were stirred with methanol (30 ml). The solids began to break up and were free flowing after a few minutes. The mixture was then filtered over Celite and combined with the original organic layer which were then concentrated under reduced pressure to give 13.74 g (106% yield) of the desired amine as an amber oil containing 10% triethylene tetramine by $^1$H NMR.

Example 9

A mixture of the N,N'-bis(aryloxyalkylene)urea (1.0 g, 2.50 mmole) and HPA (686 mg, 2.50 mmole) was heated to 170° C. under nitrogen for 1 h. The reaction was monitored by NMR for complete conversion of the dialkylene urea. The reaction was then cooled to room temperature and ExxonMobil™ Aromatic 100 solvent was added. The organic layer was washed with water, then brine. The organic layer was separated and concentrated under reduced pressure to give 660 mg (77%) of the desired amine.

What is claimed is:

1. A process for preparing an aryloxyalkylene amine compound via an aminoethylation reaction comprising:
   a) reacting an aromatic hydroxyl compound in the presence of a basic catalyst with a 2-oxazolidinone compound of the formula II to form an intermediate reaction product;

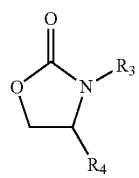

Formula II wherein $R_3$ is selected from the group consisting of hydrogen or lower alkyl having 1 to 6 carbon atoms, $R_4$ is selected from the group consisting of hydrogen, straight or branched chain alkyl having from one to six carbon atoms, phenyl, alkaryl, or arylalkyl; wherein the intermediate product contains at least one dialkylene urea compound; and
   b) reacting the intermediate product of step a) with a polyalkylene polyamine; wherein at least a portion of the dialkylene urea compound is converted to the aryloxyalkylene amine compound.

2. The process of claim 1, wherein the 2-oxazolidinone compound reactant is in molar excess to the aromatic hydroxyl compound.

3. The process of claim 2, wherein the molar ratio of aromatic hydroxyl compound to 2-oxazolidinone compound of formula II in step a) is from 1:2 to 1:1.2.

4. The process of claim 1, wherein the 2-oxazolidinone compound of formula II is formed in-situ by reacting a β-amino alcohol of the formula $NH_2$—$CHR_{10}CH_2$—OH wherein $R_{10}$ is a lower alkyl having 1 to 6 carbon atoms, phenyl, alkaryl, or arylalkyl; with a dialkyl carbonate of the formula $(R_{11}O)_2CO$ where $R_{11}$ is lower alkyl having 1 to about 6 carbon atoms.

5. The process of claim 4, wherein the molar ratio of aromatic hydroxyl compound to oxazolidinone compound of formula II in step a) is from 1:2 to 1:1.2.

6. The process of claim 1, wherein the intermediate product of step a) contains a dialkylene N, N'-bis(aryloxyalkylene) urea moiety in an amount from 10 to 50 mole %.

7. The process of claim 1, wherein the polyalkylene polyamine is of the formula $$H_2N\text{-}A\text{-}(N[R_5]\text{-}A)_x\text{—}NR_6R_7$$

wherein x is an integer of from about 0 to 10, A is an alkylene radical of from 2 to 10, $R_5$, $R_6$ and $R_7$ are independently selected from hydrogen, an alkyl from 1 to 6 carbon atoms group.

8. The process of claim 7, wherein A is selected from ethylene, 1,2-propylene and 2-2-dimethylpropylene.

9. The process of claim 7, wherein the polyalkylene polyamine is selected from the group consisting of ethylene diamine, diethylene triamine, triethylene tetraamine, tetraethylene pentamine, propylene diamine, decamethyl diamine, octamethylene diamine, diheptamethylene triamine, tripropylene tetraamine, trimethylene diamine, pentaethylene hexamine, and ditrimethylene triamine.

10. A method for improving the yield of an aryloxyalkylene amine compound prepared via an aminoethylation reaction comprising:
   a) reacting an aromatic hydroxyl compound in the presence of a basic catalyst with a 2-oxazolidinone compound of the formula II to form an intermediate reaction product;

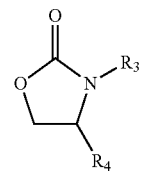

Formula II wherein $R_3$ is selected from the group consisting of hydrogen or lower alkyl having 1 to 6 carbon atoms, $R_4$ is selected from the group consisting of hydrogen, straight or branched chain alkyl having from one to six carbon atoms, phenyl, alkaryl, or arylalkyl; and thereafter
   b) reacting the intermediate product of step a) with a polyalkylene polyamine.

11. The method of claim 10, wherein the intermediate product contains at least one N, N'-bis(aryloxyalkylene) urea compound.

12. The method of claim 11, wherein during the reaction in step a) the concentration of aromatic hydroxyl compound or the concentration of at least one N, N'-bis(aryloxyalkylene) urea compound is monitored.

13. The method of claim 12, wherein during the reaction in step a) the concentration of at least one N, N'-bis(aryloxyalkylene) urea compound is monitored.

14. The method of claim 13, wherein the amount of polyalkylene amine is adjusted to lower the concentration of the compound monitored.

* * * * *